(12) United States Patent
Park et al.

(10) Patent No.: US 6,895,107 B2
(45) Date of Patent: May 17, 2005

(54) METHOD FOR SEGMENTATION AND VOLUME CALCULATION OF WHITE MATTER, GRAY MATTER, AND CEREBRAL SPINAL FLUID USING MAGNETIC RESONANCE IMAGES OF THE HUMAN BRAIN

(75) Inventors: Jong-Won Park, 389-2, Sunwha 1-Dong, Jung-ku, Taejon, 301-826 (KR); Yun-Chang Sung, Kyungbuk (KR); Chang-Jun Song, Daejon (KR); Seung-Moo Noh, Daejon (KR)

(73) Assignee: Jong-Won Park (JP)

( * ) Notice: Subject to any disclaimer, the term of this patent is extended or adjusted under 35 U.S.C. 154(b) by 594 days.

(21) Appl. No.: 09/902,506

(22) Filed: Jul. 10, 2001

(65) Prior Publication Data

US 2003/0044055 A1 Mar. 6, 2003

(51) Int. Cl.[7] ................................................ G06K 9/00
(52) U.S. Cl. ............................ 382/133; 702/23; 435/1.1
(58) Field of Search ................................. 382/128, 131, 382/133, 134; 424/9.3, 9.4; 600/410, 425, 443, 562; 73/61.48; 702/19, 21, 22, 23, 26, 27, 29, 30, 32, 137; 430/332, 333, 334, 378, 398, 541, 616; 250/461.2; 378/4, 5, 6, 8, 12, 21, 62, 83, 87, 88; 435/1.1, 40.5

(56) References Cited

U.S. PATENT DOCUMENTS 5,425,368 A * 6/1995 Brandt ........................ 600/408
6,385,479 B1 * 5/2002 Sibbitt et al. ................ 600/410
6,430,430 B1 * 8/2002 Gosche ........................ 600/410
6,751,495 B2 * 6/2004 Maier et al. ................. 600/410

* cited by examiner

Primary Examiner—Andrew W. Johns
Assistant Examiner—Shervin Nakhjavan
(74) Attorney, Agent, or Firm—Howrey Simon Arnold & White, LLP

(57) ABSTRACT

A fully-automated method for segmentation of white matter, gray matter, and cerebral spinal fluid (CSF) and for calculating their respective volumes is disclosed. The technique preferably uses a T2-weighted scan and a proton-density scan. The T2-weighted scans are used to highlight those portion of the brain corresponding to CSF. Thereafter, the proton density images are separated in CSF-containing and CSF-free portions, in accordance with the T2-weighted images. The CSF-free portion is then segmented into white matter and gray matter portions. The CSF-containing portion is further segmented into pure CSF-regions, and regions containing a mixture of gray and white matter and CSF. After CSF is segmented from this mixture, the white and gray matter and again segmented, and the respective volumes of white matter, gray matter, and CSF are calculated. A technique for determining a threshold gray scale value for segmenting the white and gray matter to assist in the visual identification of such regions is also disclosed.

55 Claims, 13 Drawing Sheets

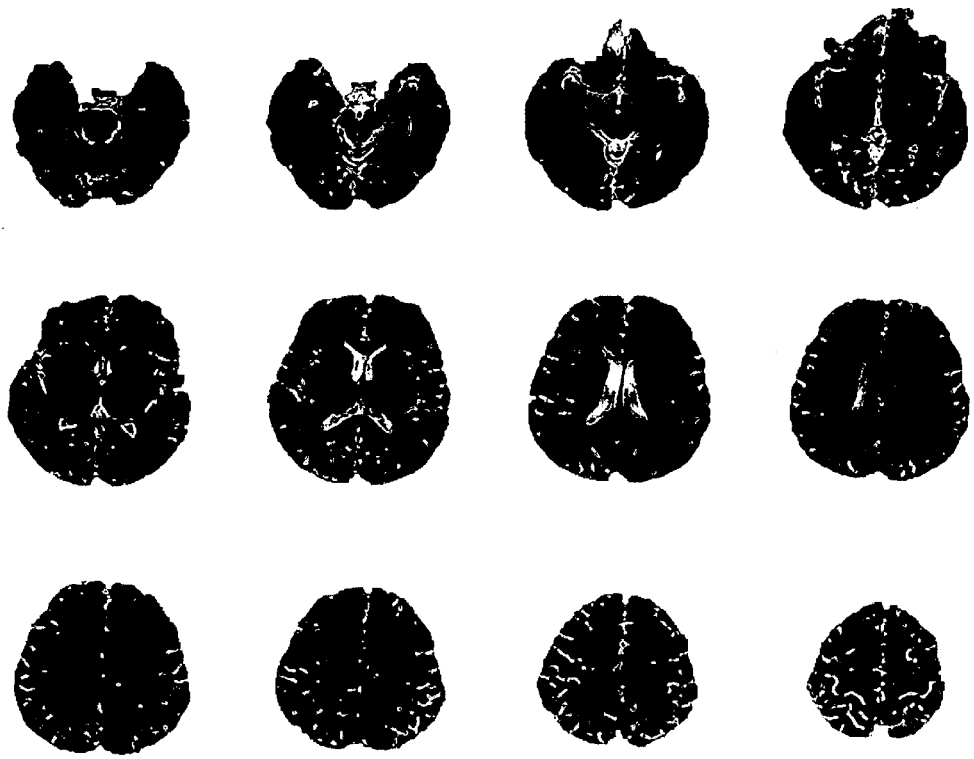
FIG. 10
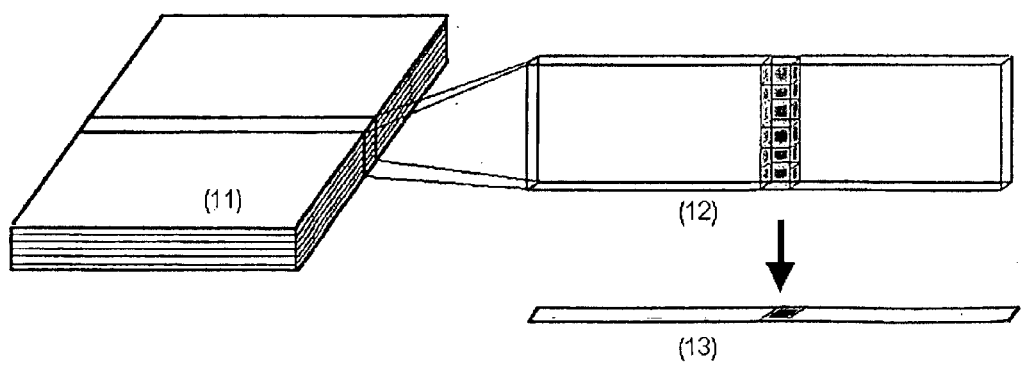

FIG. 15
  
FIG. 16
  

METHOD FOR SEGMENTATION AND VOLUME CALCULATION OF WHITE MATTER, GRAY MATTER, AND CEREBRAL SPINAL FLUID USING MAGNETIC RESONANCE IMAGES OF THE HUMAN BRAIN

BACKGROUND OF THE INVENTION

1. Field of the Invention

The present invention relates to a method for processing the images of the human brain, and more particularly to a method for segmenting and calculating the volume of the white matter, the gray matter, and the cerebral spinal fluid (CSF) in a human brain using images produced by a magnetic resonance (MR) imaging device.

2. Description of the Related Art

Medical research into the structure and operation of the human brain has been extensive, and there have been remarkable advances in medical procedures used for the discovery and cure of various cerebral diseases. In particular, the use of computed tomography (CT) and magnetic resonance (MR) imaging have been particularly useful as diagnostic tools and it is expected that the use of such images will continue into the future.

Certain degenerative cerebral diseases, such as Alzheimer's disease and cerebral palsy, involve the atrophy of the brain, and CT and/or MR images have shown to be useful in diagnosing such diseases. However, this assessment typically relies on the subjective judgment of the radiologist who visually scrutinizes such images by the naked eye. Unfortunately, there has not yet been developed a method for early diagnosis of such diseases using objective criteria involving the quantitative measurement of tissue atrophy of the white and gray matters in the brain and the resultant increase of cerebral spinal fluid (CSF).

Since the atrophy of the white and gray matters and the accompanying increase of the cerebral spinal fluid are the most common phenomena observed in patients with degenerative cerebral diseases, a quantitative calculation of the degree of atrophy in suspect tissues, monitoring the change of their volumes, and comparison of them with those of normal unaffected persons, could greatly improve the diagnosis of such diseases.

However, the complexity of the human brain and peculiarities of MR images make such a calculation difficult. Specifically, a particular voxel (i.e., the smallest until of volume resolvable in the image) is assigned one particular intensity value (i.e., a gray scale value) in the MR image, but may in fact contain partial volumes of white matter, gray matter, or CSF, giving rise to a "blurring" of the image. A method has not as yet been implemented for segmenting the respective portions of the white matter, the gray matter, and the CSF from each other in a given voxel, and hence the problem of blurring remains. This prevents the ability to accurately calculate the volume of the white matter, the gray matter, and the cerebral spinal fluid.

To date, some researchers have attempted to segment white and gray matter using T1-weighted images by semi-automatic means through manual interaction with the computer interface connected to the MR machine. However, T1-weighted images do not provide a good contrast between white and gray matter, and do not allow for a separate assessment of CSF. Additionally, the time, expense, and uncertainty of manually manipulating the MR images in this fashion makes this technique undesirable.

SUMMARY OF THE INVENTION

The disclosed embodiment of the invention involves a computer-automated technique for segmentation of white matter, gray matter, and cerebral spinal fluid (CSF) and for calculating their respective volumes. The technique preferably uses a T2-weighted scan and a proton-density scan. After extracting those portions of the scan pertaining to the inner portion of the brain, the T2-weighted scans are used to highlight those portion of the brain corresponding to CSF. Thereafter, the proton density images are separated in CSF-containing and CSF-free portions, in accordance with the T2-weighted images. The CSF-free portion is then segmented into white matter and gray matter portions. The CSF-containing portion is further segmented into pure CSF-regions, and regions containing a mixture of gray and white matter and CSF. After CSF is segmented from this mixture, the white and gray matter and again segmented, and the respective volumes of white matter, gray matter, and CSF are calculated. Moreover, a technique is disclosed for determining a threshold gray scale value for segmenting the white and gray matter to assist in the visual identification of such regions on a scan. The effect is reduced blurring of these resulting image. The disclose technique thus provides a quantitative, cost-efficient, fully automated system for ascertaining and monitoring these structures of the brain.

BRIEF DESCRIPTION OF THE DRAWINGS

FIG. 9 shows FIG. 3, wherein the inside of the brain has been extracted.

FIG. 10 shows an illustration of image slices 11, voxels 12, and pixels 13.

FIG. 15 shows a proton-density image slice in which the CSF portion has been extracted.

FIG. 16 shows the CSF portion extracted from the proton-density image slice of FIG. 15.

DETAILED DESCRIPTION OF THE PREFERRED EMBODIMENTS

In the disclosure that follows, in the interest of clarity, not all features of actual implementations are described. It will of course be appreciated that in the development of any such actual implementation, as in any such project, numerous engineering and design decisions must be made to achieve the developers' specific goals and subgoals (e.g., compliance with mechanical- and business-related constraints), which will vary from one implementation to another. Moreover, attention will necessarily be paid to proper engineering and design practices appropriate for the environment in question. It will be appreciated that such a development effort might be complex and time-consuming, but would nevertheless be a routine undertaking for those of skill in the art. For example, while the disclosed technique involves an automatic assessment of image file data, and manipulation of such data by mathematical and statistical analysis, such analysis is easily achieved by a suitable computer programmed to so operate.

Figure 1:
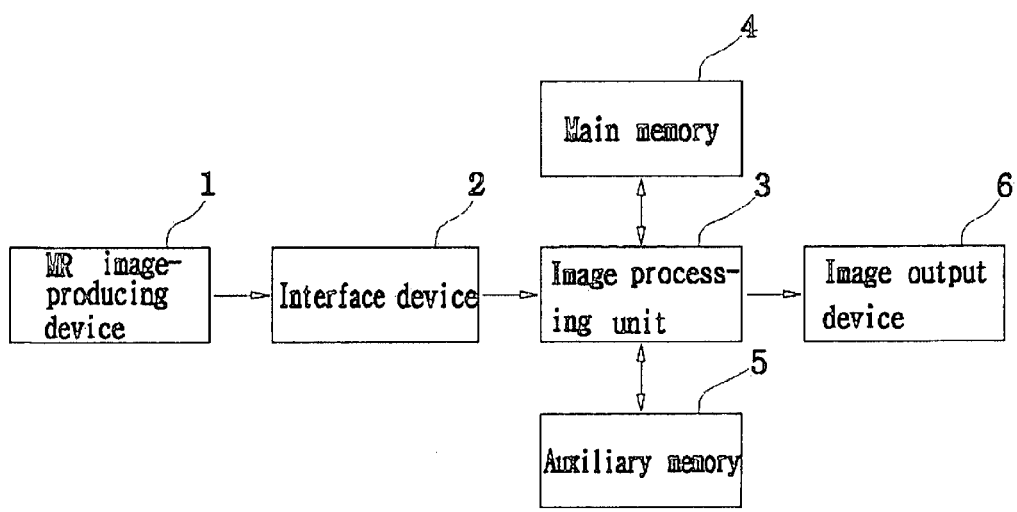
FIG. 1 shows a block diagram of a device for implementing the present invention.

FIG. 1 is a block diagram of a device useful for controlling and processing the images produced by a MR image-producing device. The image file provided by an MR image-producing device 1 is conveyed via an interface device 2 to an image-processing unit 3. Said image processing unit 3 stores the conveyed image data in its main memory 4, and loads the necessary programs for segmentation and volume calculation routines disclosed herein from auxiliary memory 4. The images, either in manipulated or raw form output onto an image output device 6, such as a computer monitor and/or printer. An image database (not shown) stores the data concerning the segmentation of white and gray matter and CFS, their calculated volumes, and other relevant data, including the patient's name, sex, age, date, etc.

Image-producing device 1 can constitute a CT or MR machine, or other machine suitable for producing an image of the brain. However, the present disclosure presents an analysis of MR images.

Figure 2:
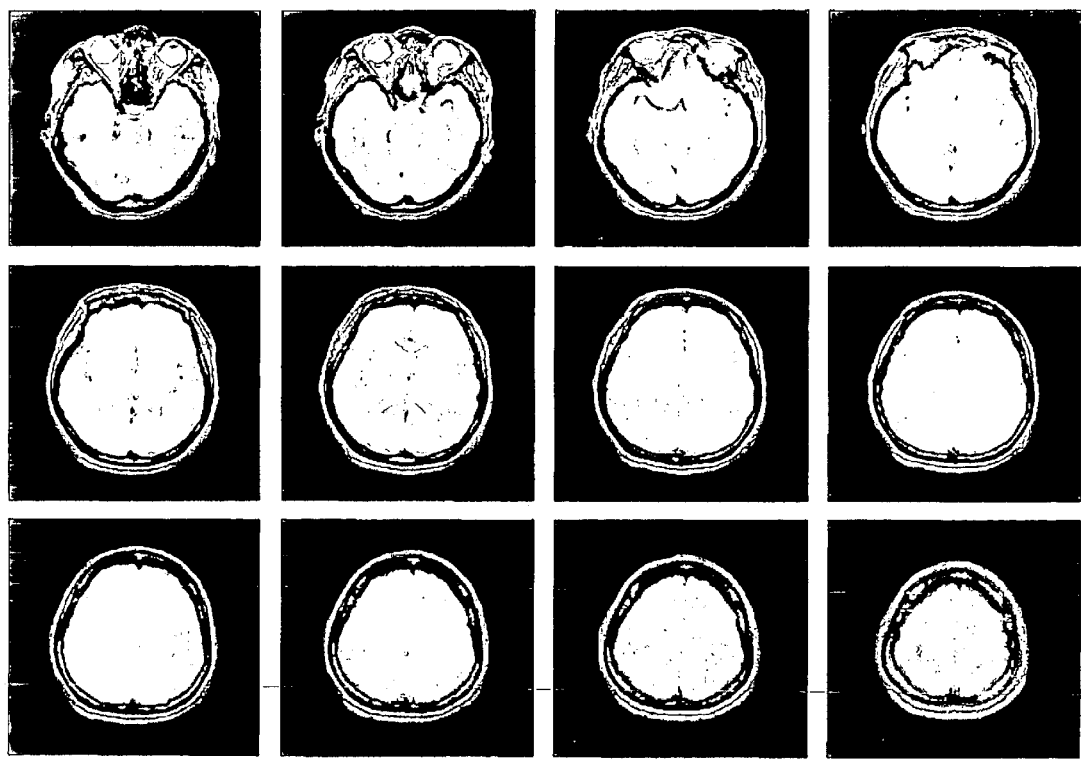
FIG. 2 shows proton-density slice images of a human brain.

Referring to FIG. 2, the size of an MR image slice (of which twelve are shown) is 256 by 256 pixels, in which each pixel is represented by a gray scale value ranging from 0 to 4,095. Each pixel comprises 2 bytes of information, and hence one image slice file requires 256×256×2=128 Kbytes of storage capacity. The header of an image slice file can also contain various data concerning the image, including information about the patient. In a preferred embodiment, an image slice file is converted into files of an 8-bit PGM (portable gray map) style, which is thereafter used in analysis. Through this conversion process, each pixel is represented by a gray scale ranging from 0 to 255.

Figure 3:
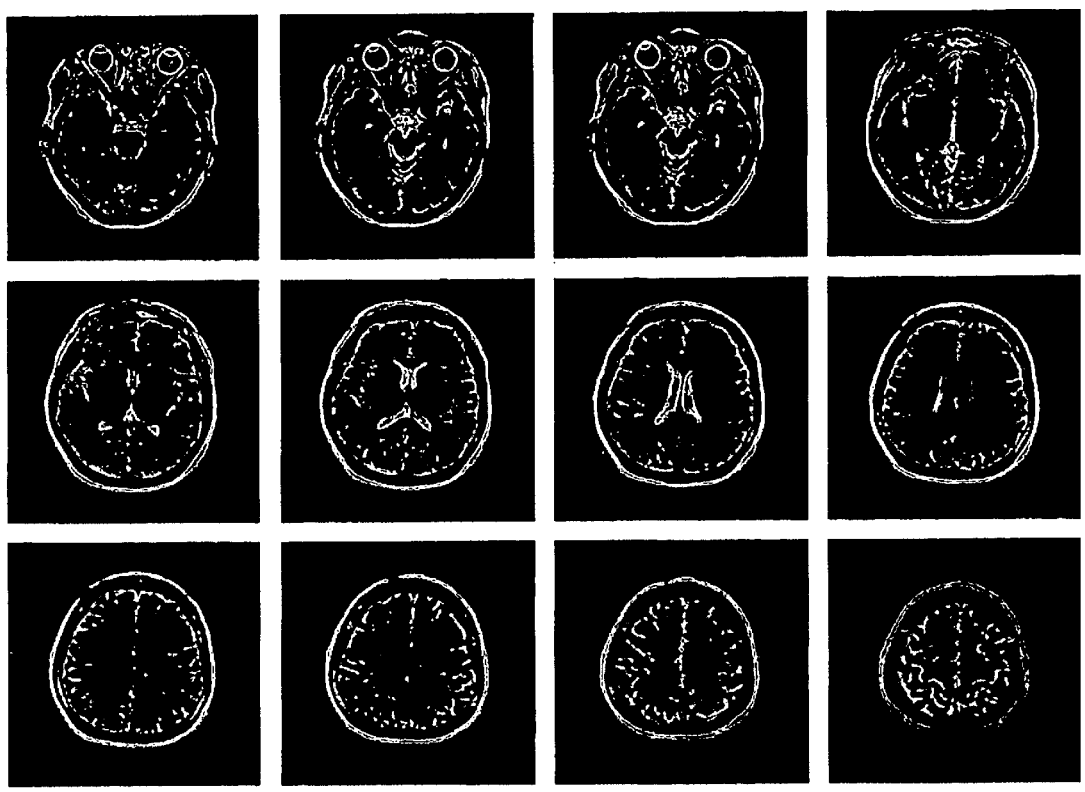
FIG. 3 shows T2-weighted image slices of a human brain.

In a preferred embodiment, the disclosed technique involves taking a proton-density image and a T2-weighted image of the brain, shown in FIGS. 2 and 3 respectively, such scanning procedures being known to those skilled in the art of MR imaging. The image slices start at the height of the eye (starting with the upper-left image in FIGS. 2 and 3) and progress upwards (from left to right) at, for example, 5 millimeter (mm) increments. Using slices of this height, it takes approximately 15 slices to image the entire brain. Hence, the entire scanned area comprises 256×256×15 voxels. It can be seen that the lower-most slice encompasses a relatively small area of the cerebrum, including parts of the cerebellum, the eyes, the brain stem, and other structures. As the scan progresses upwards, the middle slices, taken of the center of the brain, are the largest in area and appear roughly as butterfly-shaped ellipses. As the scan approaches the top of the head, the images become smaller and smaller.

One will notice that the proton-density images (FIG. 2) and the T2-weighted images (FIG. 3) appear different in hue. The T2-weighted images generally appear darker than the proton-density images, but in the regions of the brain and spinal cord they appear relatively lighter than the latter. Accordingly, the T2-weighted images are more useful in the extraction in the data concerning the CFS. However, the contrast between white and gray matter is not as clear on these images. By contrast, the proton-density images provide a sharper contrast between white and gray matter, although in these images it is more difficult to distinguish the portions of the brain and spinal cord. Accordingly, in the preferred embodiment of the invention, the proton-density images are generally used in the segmentation of white and gray matter, while the T2-weighted images are used for determining those locations of the brain containing CSF.

Prior to analysis of the images, it is necessary to remove from the proton-density images of FIG. 2 those portions of the image that have no relevance to the brain, including the dark background, the cortex, and the layer of fat which surrounds it.

Figure 4:
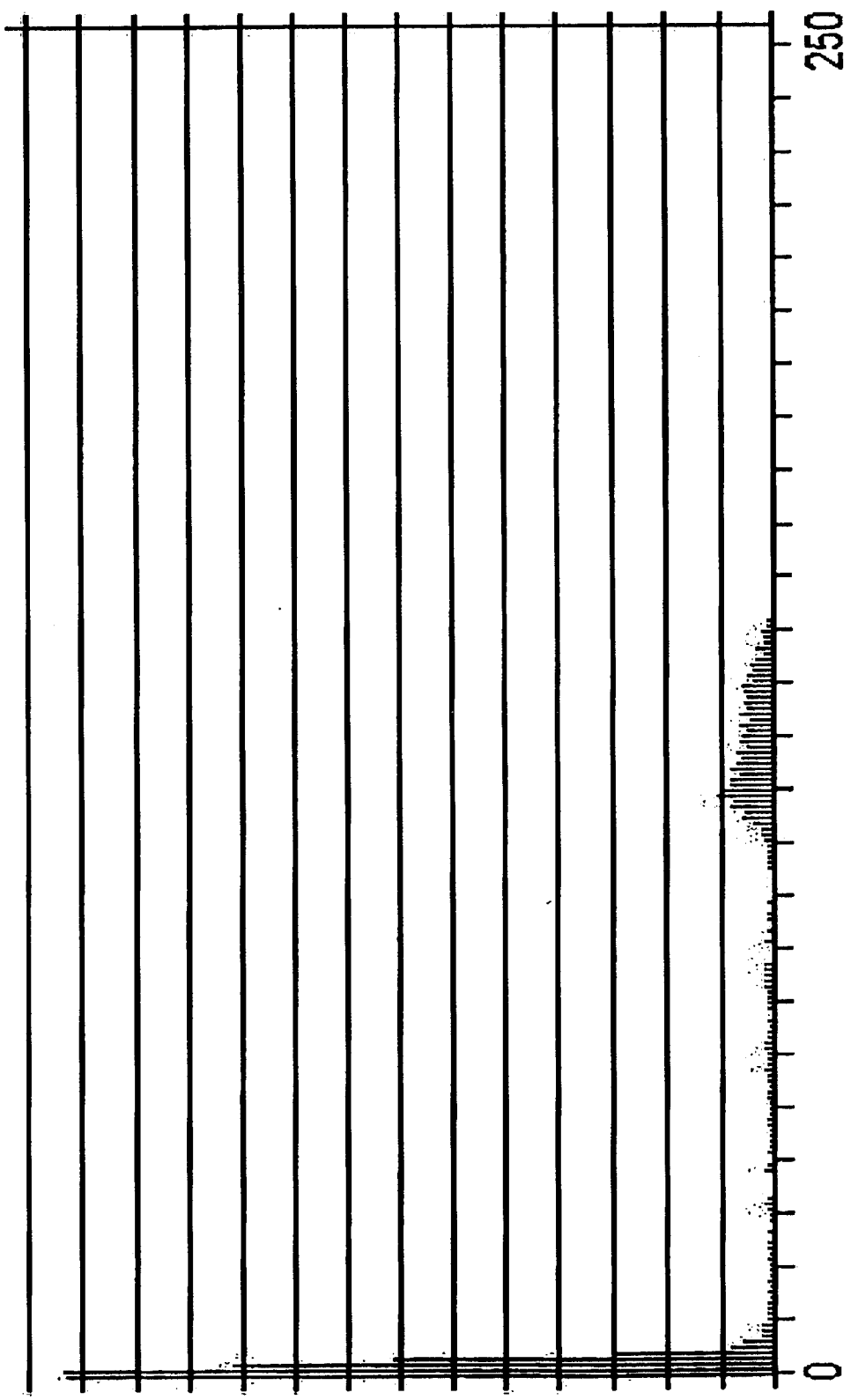
FIG. 4 shows a histogram for the proton-density image.

The removal of the dark background is performed as follows. First, a histogram of each slice is compiled. FIG. 4 shows a graphical histogram for the eighth slice of FIG. 2, and shows the number of pixels with a given gray scale value on the vertical axis and the gray scale values (i.e., from 0 to 255) on the horizontal axis. As one would expect, the histogram shows, at the left-most peak, that the image slice has a large number of dark pixels, ranging from gray scale values from 0 to about 10, and representing, for example, the dark background and the layer of fat enveloping the inside of the brain. Likewise the histogram of pixels having a gray scale of about 90 or more, and which represent the image of the inner part of the brain, appear as a roughly Gaussian-shaped peak in the middle of the histogram.

Figure 5:
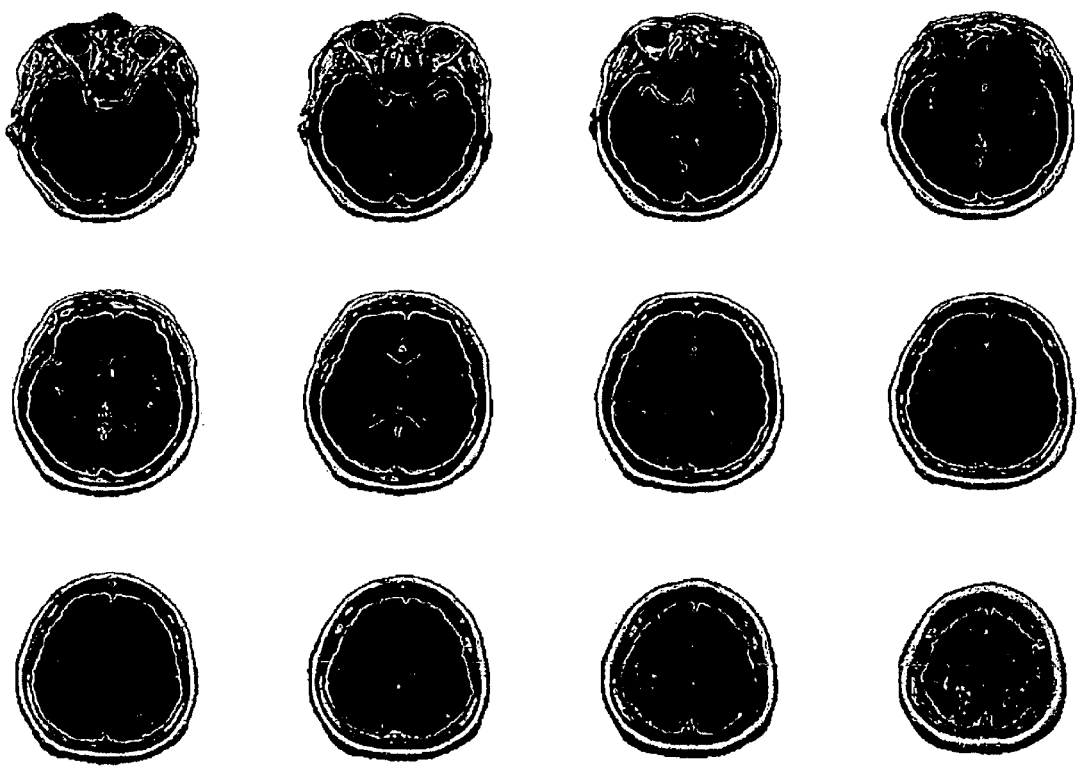
FIG. 5 shows FIG. 2 with the dark background removed using the information provided by the histogram of FIG. 4.

The sharp distribution between these two peaks allows for the dark background to be removed from the image slice. The pixels, starting with one random pixel 0, 0 at the corner of the image slice, were traced by the "4-connectivity rule" to see if they were bounded in the image slice by pixels having a gray scale greater than 90, and if not, they were removed from the image. It should be noted that the use of the 4-connectivity rule will keep the dark fatty layer as part of the image, even though the gray scale values for those pixels is less than 90, because they are not related to those pixels which constitute the dark background and otherwise are bound by suitably light pixels. Of course, one skilled in the art will recognize that generation of a histogram, discerning the two peaks in the histogram, and removal of the background dark pixels is preferably performed algorithmically with the assistance of a computer and a suitable data analysis program. FIG. 5 shows the resulting proton-density image with the dark background removed as explained above.

The gray value distributions of the pixels in an image slice can differ from one person to another, and can vary from slice to slice in the scan of a given person. This is seen in FIG. 5, which shows that the slices are generally lighter as the MR scan progress to the top of the patient's head. This unwanted artifact from the MR scan creates problems in the subsequent steps of the disclosed technique. First, in the upper slices, the contrast between the inner part of the brain and the darker fat layer which envelops it are not suitably sharp, making it difficult to subsequently extract from the image the inner portion of the brain, as will be subsequently described. Second, the contrast between the white and gray matter in the inner portion of the brain is likewise not as sharp as would be desirable to effect accurate segmentation of the white and gray matter.

Figure 6:
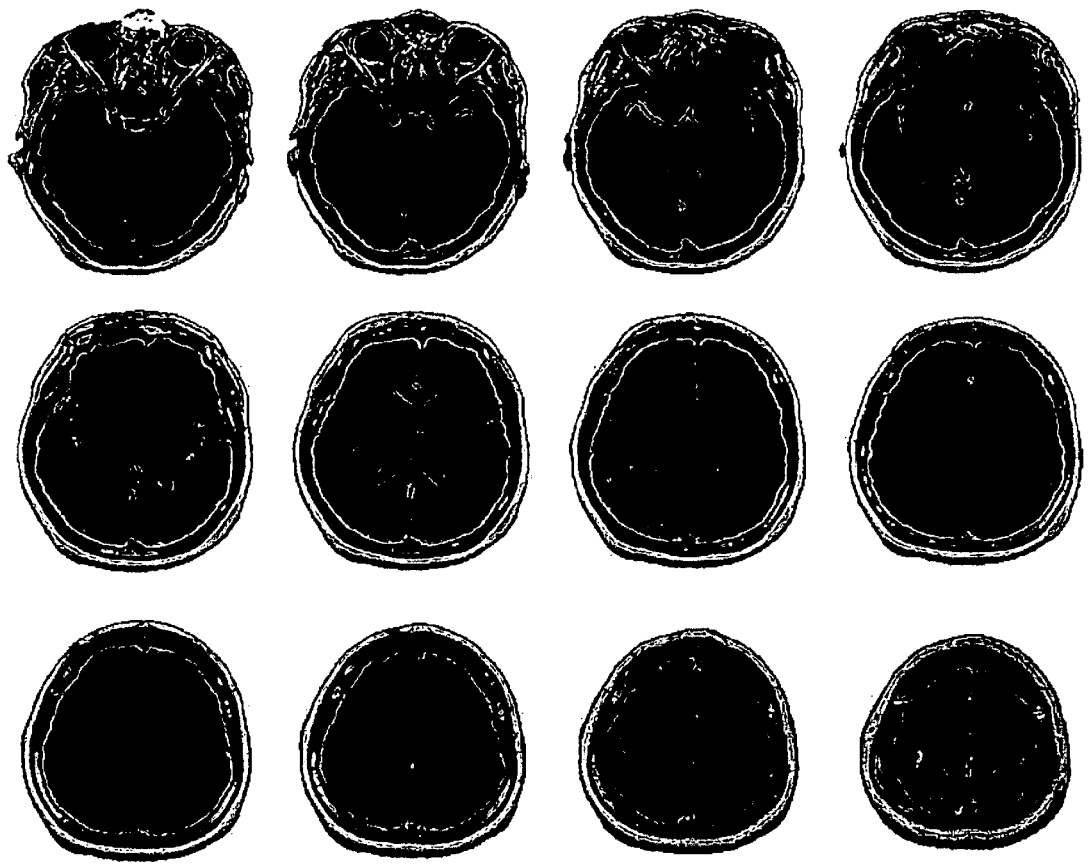
FIG. 6 shows FIG. 5 with the images slices adjusted to a uniform gray value.

Accordingly, at this point, it is generally deemed advisable to adjust the contrast of the various slices to make them more uniform. This can be preferably performed by adjusting the average gray scale value for the inner region of the human brain (corresponding to the central peak on the histogram of FIG. 4) to a gray scale value of, for example, 120, for each image slice. When the image slices are adjusted in this fashion, suitable contrasts between the fat layer and the inner portion of the brain, and between the white and gray matter in the inner portion of the brain, are realized. FIG. 6 shows the image slices adjusted in this fashion, and it can be seen that the images now appear more uniform in intensity.

Figure 7:
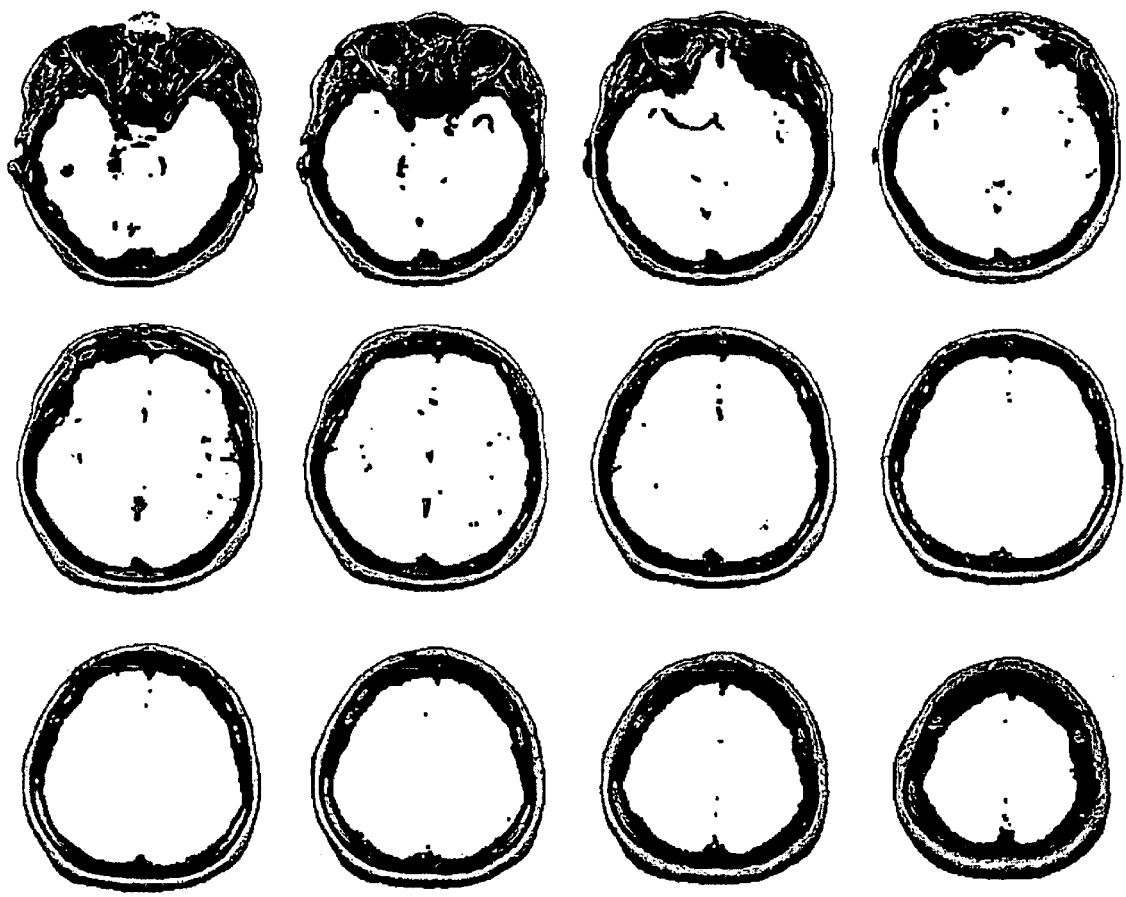
FIG. 7 shows FIG. 6, wherein the inside of the brain has been traced for each of the images.

Following the adjustment of the gray scales of the image slices, the extraction of the inner part of the brain is performed. After the adjustment, the inner part of the brain comes to have, on the whole, a gray value of 90 or more, and is encircled by an elliptical layer of fat with a gray scale value of 90 or less. Accordingly, if the pixels having gray scale values of 90 and up are traced from some pixel corresponding to the inner part of the brain by the 4-connectivity practice, then only the portions of the fat layer and beyond, and the pieces of the cortex in the inner portion of the brain are left behind, as shown in FIG. 7. These dark portions of the cortex in the inner portion of the brain should be identified and traced using the 4-connectivity method and included for purposes of further analysis. When the fat layer and outside structures are excluded from the image, but the dark regions in the inner portion of the brain are included, the image of FIG. 8 results, which comprises a complete image of the inner portion of the brain, and which will be analyzed and segmented by the disclosed technique. The T2-wieghted image of FIG. 3 may be similarly treated as the proton-density images, rendering the images of FIG. 9.

Figure 8:
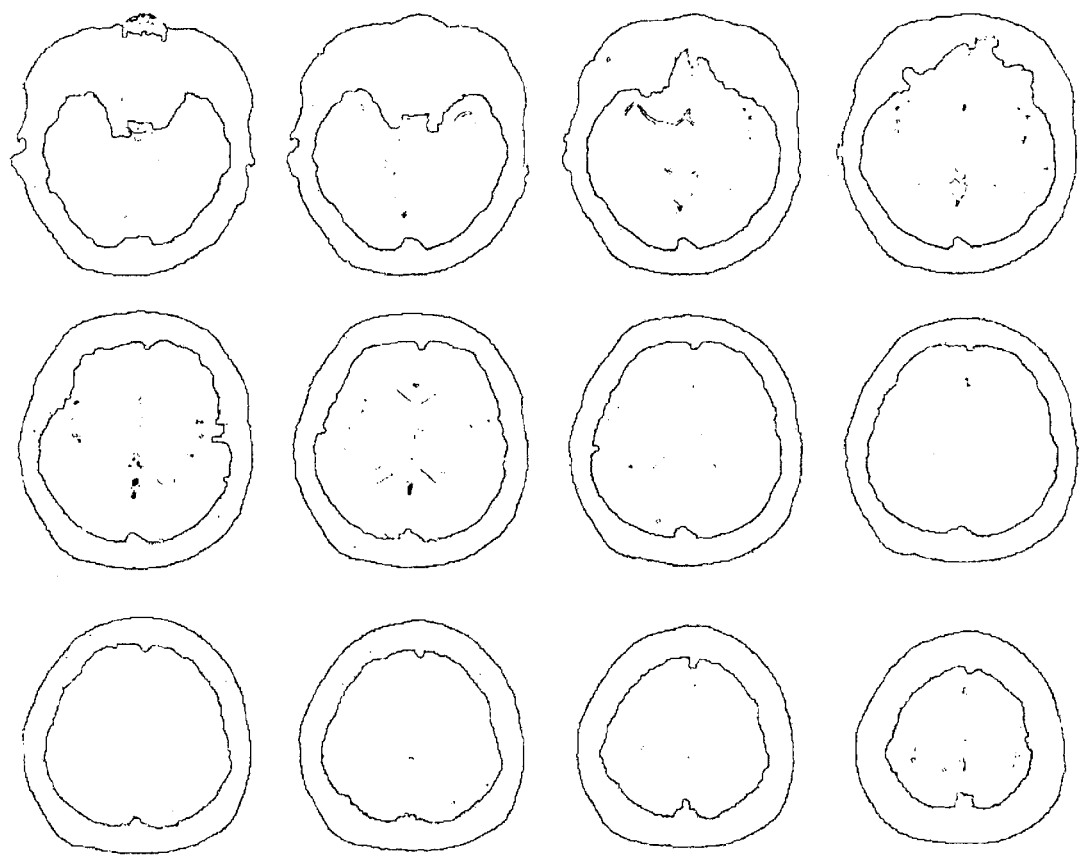
FIG. 8 shows FIG. 7, wherein the inside of the brain has been extracted.

The extraction of white matter, gray matter, and CSF, and the calculation of their respective volumes are performed using the images like FIGS. 8 and 9 that only encompass the inner portion of the brain. The images of FIG. 8 will generally be used to segment the white and gray matters and calculate their volumes while the images of FIG. 9 will generally be used for the extraction of CSF data and calculation of its volume.

The disclosed procedure for calculating the volume of white matter, gray matter, and CSF requires proper segmentation of these materials, taking into consideration of their respective partial volumes in a given voxel. This problem is exacerbated by the use of larger voxels. Usually, the MR imaging device scans the human body by a finite thickness (e.g., from 3 mm to 10 mm) to produce image slices. This thickness sets the height of the voxels and is thus proportional to a voxel's volume. While a smaller voxel stands a better chance of containing either fat or water alone, a larger one will more likely contain both, and accordingly the gray scale value of that larger voxel will have an intensity proportional to the amount of fat and water contained in it. The result is a blurring of the white and gray matters and the CSF in the resulting image.

Figure 11A:
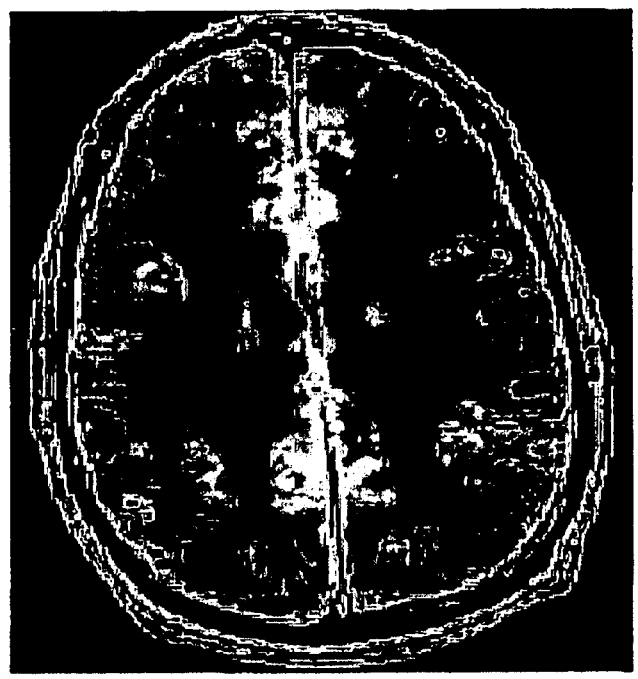
FIG. 11a shows a proton-density image taken of a 3 mm-thick image slice.
Figure 11B:
FIG. 11b shows that same image as that in FIG. 11a, but taken of a 10 mm-thick image slice to show the effect of blurring.

An example of this blurring is shown in FIGS. 11a and 11b, which shows a proton-density image slice of a brain taken with slice thicknesses of 3 mm and 10 mm respectively. It is easily seen that the image of FIG. 11a, containing smaller voxels, is much sharper than the relatively blurred image of FIG. 11b, containing larger voxels. This is due to the more likely co-existence of white matter, gray matter, CSF, etc., in the larger voxel. Such blurring of these constituents in the larger voxel generally cannot be helped, as the MR imaging device merely records the average energy being emitted by the tissues during magnetic stimulation and cannot discern the relative amounts of a given tissue that might be present in the voxel.

Figure 12:
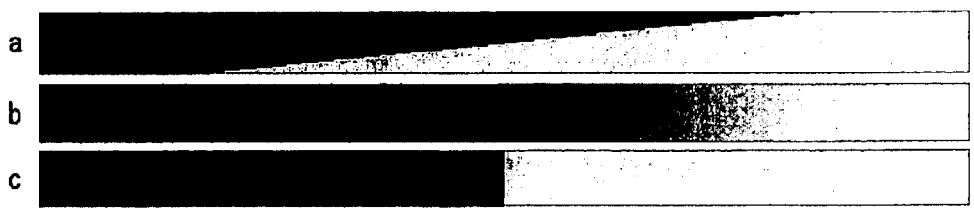
FIG. 12 shows a simple example of the problem of partial volumes of tissues, the blurring that results in the MR image, and determining a threshold to reduce such blurring.

As a further illustration of blurring, and a method for segmenting two materials to prevent blurring, is shown in FIG. 12. FIG. 12a show the actual distribution of two tissues in a portion of an image slice. In this portion, the left side is entirely made up of tissue X, while the right side is entirely made up of tissue Y, with a mixture of the two being present in the middle of this portion. FIG. 12b show how an MR image of this portion would appear. As would be expected, the image is dark on the left side and gradually (i.e., in a blurred manner) shifts to a lighter color on the right side. When a suitable gray scale threshold is picked, the image in FIG. 12b can be segmented to produce a sharp image indicative of whether a given pixel or voxel contains a predominance of tissue X or tissue Y, as shown in FIG. 12c. Of course, such segmentation as illustrated in FIG. 12c does not accurately portray the actual tissues that are present at a given pixel or voxel, but it does allow for an accurate calculation of the respective volumes of tissue X and tissue Y.

For example, assume that a first tissue having a gray scale value of y1 and second tissue having a gray scale of y2 exist in a given voxel, with the first tissue comprising z % of the voxel and the second tissue comprising the remaining (100−z) % of the voxel. The resulting gray scale value, G, of that voxel will comprise a weighted average of the relative compositions of these two gray scale value according to the following equation:

$$G = y1 \times \frac{z}{100} + y2 \times \left(1 - \frac{z}{100}\right)$$

Working backward from G, the equation can be solved for z, and hence the relative volumes of the first tissue (z %) and the second tissue ((100−z) %) can be calculated.

Using this method, it is possible to use an MR image, such as the image in FIG. 12b, to calculate respective volumes of each component in a given pixel or voxel, and to determine the gray scale value for segmentation of the two components in a region which is blurred by a mixture of the components, as shown in FIG. 12c. Such a gray value is termed the "threshold" value.

This volume calculation process is now illustrated using the third, eighth, and twelfth image slices, although the other image slices would be treated in a similar manner.

First, the portion of the inner part of the brain containing CSF is determined using of T2-weighted images of FIG. 9. Those portions of the T2-wieghted images containing CSF are generally those portions that are lighter in color.

Figure 13:
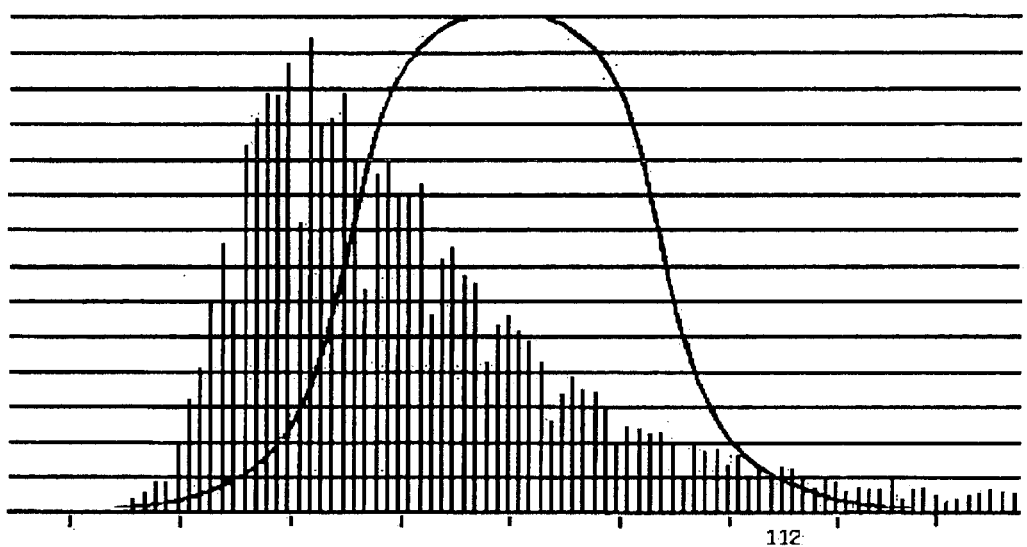
FIG. 13 shows the determination of the lowest gray scale value for CSF in a T2-weighted image slice.
Figure 14:
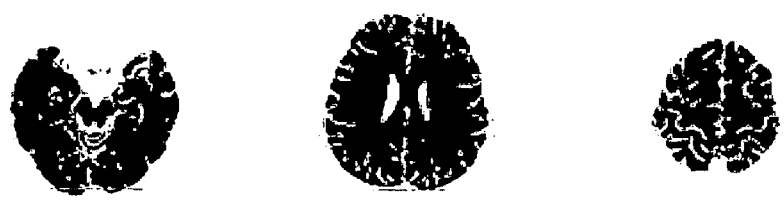
FIG. 14 shows a T2-weighted slice in which the CSF portion has been extracted.

However, as with the proton-density images, the T2-weighted images also vary in average gray scale values from slice to slice. To deal with this variation, and to pick an accurate gray scale value threshold above which a pixel in the T2-weighted images will be considered as containing CSF, a histogram of the T2-weighted image of the inner part of the brain, as shown in FIG. 9, is plotted and compared against a Gaussian curve, which is shown in FIG. 13 for the eighth image slice. The gray scale value at which the histogram value first exceeds the Gaussian curve is chosen as the CSF threshold, which in the example shown is a gray scale value of 112. Accordingly, those pixels in the T2-wieghted image having a gray scale value of greater than 112 are deemed to contain, at least partially, CSF, while other pixels are considered to contain only white and gray matter. This same procedure is then performed on each of the slices, to increase accuracy and remove inconsistency in gray scale that might exist between the slices. With this division of the various pixels made complete, the T2-weighted images can have the CSF-containing pixels removed therefrom, as shown for the third, eighth, and twelfth images in FIG. 14.

The portions (i.e., pixel or voxels) of the brain containing CSF having been so determined using the T2-wieghted images, the proton-density images are next divided into CSF-free portions and CSF-containing portions, as shown in FIGS. 15 and 16 respectively. FIG. 15 shows the proton-density images for those pixels corresponding to the CSF-free pixels from the T2-weighted images (i.e., FIG. 14). FIG. 16, by contrast contains the remaining portions of the proton-density images that correspond to the CSF-containing pixels from the T2-weighted images.

Figure 17:
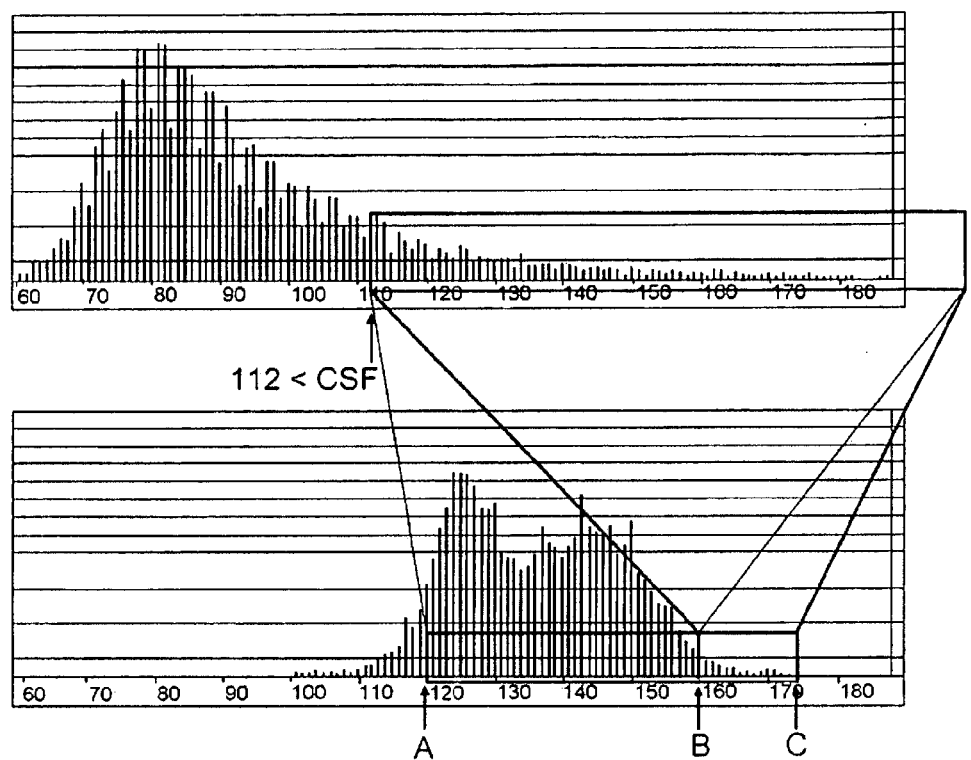
FIG. 17 shows histograms showing the relation in gray scale values between the CSF portion in a T2-weighted image and its corresponding proton-density image.

The CSF portions extracted from the proton-density images have distributions of gray scale values different from those in the T2-weighted images. While the CSF extracted from the T2-weighted images appears relatively light, it will be darker if white and gray matter are mixed with it, the images being darker in proportion to the quantities of these mixed contents. FIG. 17 shows the histograms for the CSF portions extracted from the T2-wieghted images of FIG. 14 (bottom), and the CSF portions extracted from the proton-density images as shown in FIG. 16 (top).

Figure 18:
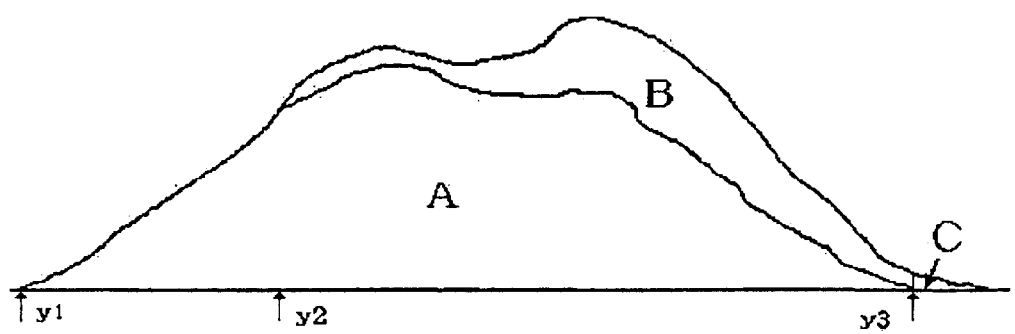
FIG. 18 shows a histogram for a proton-density image, including both CSF free and CSF containing portions.
Figure 19:
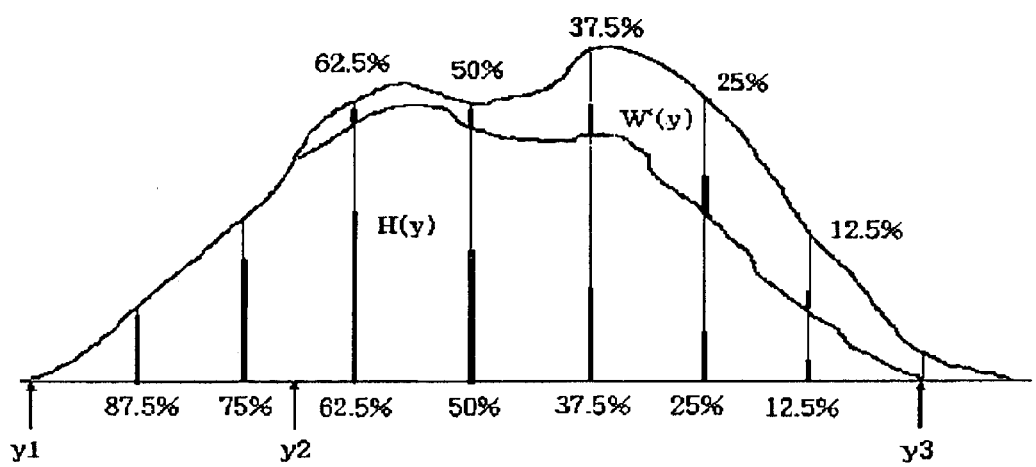
FIG. 19 shows the histogram of FIG. 18 annotated to illustrate the calculation of white matter.

FIG. 18 shows a proton-density image histogram, H(G), from which the CSF portions have been removed (region A, e.g., an image from FIG. 15), and the histogram for the thus extracted CSF portions, W(G) (regions B and C, e.g., an image from FIG. 16), which is laid on top of the histogram of region A. Region A contains a combination of white and gray matter, which must be segmented as will be explained shortly. Region B contains a combination of white and gray matter and CSF, and also must be segmented. Region C contains pure CSF. From an analysis of these histograms, three variables y1, y2, and y3 can be ascertained. y1 denotes the lowest gray scale value that white matter can have, y2 denotes that lowest gray scale that CSF-containing portions can have, and y3 denotes the highest gray scale value that gray matter can have and also denotes lowest gray scale value that pure CSF can have.

The process of segmentation of the white and gray matter within Region A is now described. As noted earlier, if white matter having a gray scale value of y1 occupies z % of a voxel, and gray matter having a gray scale value of y3 occupies the remaining (100–z) % of the voxel, (which should be the case in Region A as it only contains white and gray matter) the resulting "blurred" gray scale value for the voxel will be:

$$G = y1 \times \frac{z}{100} + y3 \times \left(1 - \frac{z}{100}\right)$$

If the gray scale value G falls half-way between y1 and y3, then, of the pixels showing such a gray value, 50% can be assumed to be white matter the remaining 50% as gray matter. Accordingly, the number of the pixels for the partial volume of the white matter in Region A can be calculated as:

$$PV1 = \int_{y1}^{y3} H\left(y1 \times \frac{z}{100} + y3 \times \left(1 - \frac{z}{100}\right)\right) \times \frac{z}{100} dy$$

Supposing W(G) to be the distribution Regions B and C, the number of pixels containing pure CSF, i.e. in Region C extending from y3 to maximum gray scale value 255, are calculated as follows:

$$PCSF1 = \int_{y3}^{255} W(G) dy$$

The partial volume of the white matter must be calculated for Region B also, which contains a mixture of white and gray matter and CSF. To accomplish this, pixels containing a partial volume of the CSF must be segmented and removed. In the case where the CSF with a gray scale value of y3 occupies z % of a voxel, and the white and the gray matters with a gray scale value of y2 occupy the remaining (100–z) % of the voxel, the resulting "blurred" gray scale value for the voxel will be:

$$G = y2 \times \left(1 - \frac{z}{100}\right) + y3 \times \frac{z}{100}$$

Thus, the number of the pixels corresponding to the partial volume of the CSF in each gray value from y2 to y3 in Region B is calculated as follows:

$$PCSF2 = \int_{y2}^{y3} W\left(y2 \times \left(1 - \frac{z}{100}\right) + y3 \times \frac{z}{100}\right) \times \frac{z}{100} dy$$

Accordingly, PAC=PCSF1+PCSF2, is the total number of pixels corresponding to CSF.

It is now possible to segment the number of pixels corresponding to white matter and gray matter in Region B. Suppose W'(G) is the distribution function of Region B after the pixels identified as CSF have been removed from W(G). The number of the pixels for the partial volume of the white matter in Region B can be calculated as:

$$PV2 = \int_{y1}^{y3} W'\left(y1 \times \frac{z}{100} + y3 \times \left(1 - \frac{z}{100}\right)\right) \times \frac{z}{100} dy$$

Accordingly, PV=PV1+PV2, is the total number of pixels corresponding to white matter in a given image. The remaining pixels in the image are gray matter, which is calculated as:

$$PG = \left[\int_{y1}^{y3} H(G) dy + \int_{y2}^{y3} W'(G) dy\right] - PV$$

In a given proton-density image, after the pixels corresponding to pure and partial volume CSF have been removed, the gray scale threshold value for segmentation of white matter and gray matter can be ascertained. If T denotes a histogram for the proton-density image, the gray value t, at which T, integrated from y1 to t, is greater than or equal to the number of white matter pixels, i.e., PV=PV1+PV2, is picked to serve as the gray scale value threshold to delineate white and gray matter:

$$PV1 + PV2 \leq \int_{y1}^{t} T(y)dy$$

Figure 20:
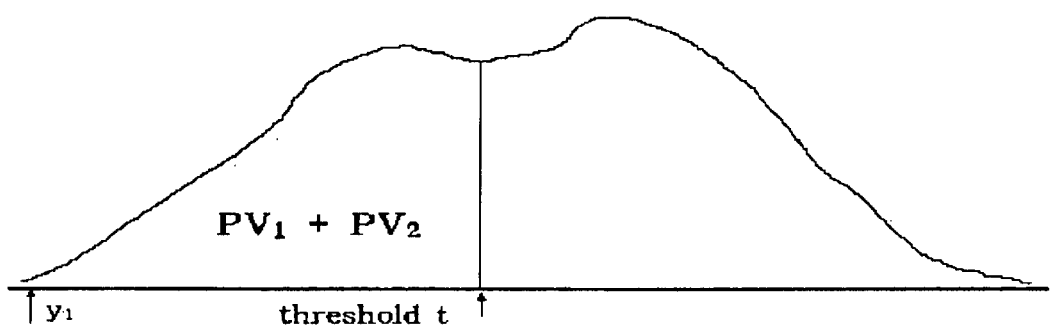
FIG. 20 shows the histogram of FIG. 18 to graphically illustrate the determination of a gray scale threshold value for segmenting white and gray matter.
Figure 21:
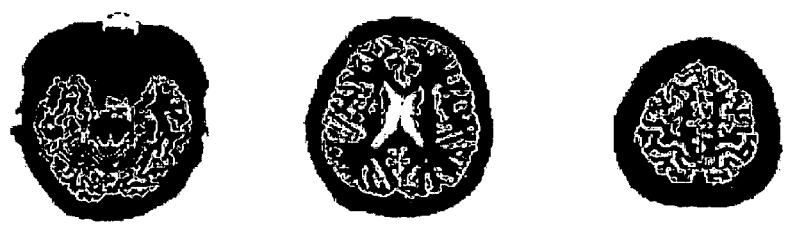
FIG. 21 shows is a proton-density image modified to shows the segmented portions of white matter, gray matter, and CSF.

FIG. 20 shows this threshold determination graphically. As previously mentioned, those pixels in the proton-density image corresponding to CSF have already been identified (see FIG. 16 and its accompanying discussion above). The remaining pixels are then sorted as pertaining to white or gray matter by comparing their gray scale value in the proton-density image to t. Accordingly, an image can be produced in which the white matter pixels are printed in a dark hue, the gray matter is printed in a gray hue, and the CSF is printed in a white hue. FIG. 21 shows such an image, which is much less blurred than the raw images coming from the MR machine.

With the pixels in each slice segmented as either gray matter, white matter, or CSF, it is possible to calculate their respective volumes by simply summing up the number of pixels for each image slice and using other information contained in the header file, such as the sizes of the voxels. This volume is represented mathematically as:

$$V = \sum_{i=1}^{N-1} (((W_p \times X \times Y) \text{ of } S_i + (W_p \times X \times Y) \text{ of } S_{i+1})/2) \times D$$

where, N=the number of the treated MR image slices, Si=slice numbers, Wp=the number of pixels constituting the extracted components, X and Y=the lateral and vertical lengths of a pixel, and D=the thickness of an image slice.

Thus disclosed is a method for calculating the volume of white matter, gray matter, and CSF in the human brain using image slices of a known thickness. Also disclosed is a method for segmenting the white matter, gray matter, and the CSF. By use of this technique, it is hoped possible to prepare statistics concerning the make up and volume of these constituents in the healthy brain for comparison with similar data from those patients suffering from degenerative brain diseases. It is hoped that such this technique will allow for early detection, and an accurate basis for monitoring the progression, of such diseases.

Although specific embodiments of the invention have been disclosed herein in some detail, this has been done solely for the purposes of illustrating various aspects and features of the invention, and is not intended to be limiting with respect to the scope of the invention. It is contemplated that various substitutions, alterations, and/or modifications, including but not limited to those design alternatives which might have been specifically noted in this disclosure, may be made to the disclosed embodiment without departing from the spirit and scope of the invention as defined in the appended claims.

What is claimed is:

1. A method of determining the amount of a first component, a second component, and a third components in a tissue, the method utilizing a first image and a second image of the tissue, the images being comprised of pixels with gray scale values, wherein the first image accentuates the difference between the first and second components, and wherein the second image accentuates the differences between the third component and the first and second components, the method comprising:
   (a) using the second image to determine which pixels contain the third component;
   (b) modifying the first image by subtracting the pixels containing the third component from the first image; and
   (c) using the modified first image to determine which pixels therein contain a majority of the first component, and which pixels therein contain a majority of the second component.

2. The method of claim 1, wherein the tissue is a brain, the first component is white matter, the second components is gray matter, and the third matter is cerebral spinal fluid.

3. The method of claim 2, wherein the first and second images are pre-processed to remove all areas outside of and including a fatty layer that surrounds the brain.

4. The method of claim 1, wherein the first image is produced by a proton density magnetic resonance imaging scan, and the second image is produced by a T2-weighted magnetic resonance imaging scan.

5. The method of claim 1, wherein using the second image to determine which pixels contain the third component includes statistically determining a threshold gray scale value above which a pixel will be deemed to contain the third component.

6. The method of claim 5, wherein the statistical determination includes comparison of a histogram of gray scale value of the pixels of the second image with a Gaussian distribution, and wherein the threshold gray scale value is determined to be that value that first exceeds the Guassian distribution.

7. The method of claim 1, wherein step (c) includes assessing a histogram, H(G), of gray scale values of the first component and second component, wherein G constitutes a weighted average gray scale of a given pixel such that $G = y1 \times z/100 + y3 \times (1-z/100)$, wherein the first component occupies z % of the pixel, and wherein the H(G) is bounded by gray scale values y1 and y3, and wherein the number of pixels containing a majority of the first component equals:

$$\int_{y1}^{y3} H\left(y1 \times \frac{z}{100} + y3 \times \left(1 - \frac{z}{100}\right)\right) \times \frac{z}{100} dy.$$

8. The method of claim 1, wherein the first and second images constitutes image slices of a particular volume of the tissue.

9. The method of claim 8, wherein the method is repeated for several different image slices each representing a different volume of the tissue.

10. The method of claim 9, wherein the first and second images obtained for each different volume of tissue are normalized to a uniform gray scale.

11. A method of determining the amount of a first component, a second component, and a third components in a tissue, the method comprising:
   (a) taking a first gray scale image and a second gray scale image of the tissue, the first and second images containing corresponding pixels with gray scale values;
   (b) using the gray scale value of the pixels of the first and second images to calculate the pixels that correspond to a majority of the first component, a majority of the second component, and a majority of the third component;

(c) computing the amount of the first component by summing the number of pixels corresponding to a majority of the first component, computing the amount of the second component by summing the number of pixels corresponding to a majority of the second component, and computing the amount of the third component by summing the number of pixels corresponding to a majority of the third component.

12. The method of claim 11, wherein the first image accentuates the difference between the first and second components, and wherein the second image accentuates the differences between the third component and the first and second components.

13. The method of claim 11, wherein the tissue is a brain, the first component is white matter, the second components is gray matter, and the third matter is cerebral spinal fluid.

14. The method of claim 13, wherein the first and second images are pre-processed to remove all areas outside of and including a fatty layer that surrounds the brain.

15. The method of claim 11, wherein the first image is produced by a proton density magnetic resonance imaging scan, and the second image is produced by a T2-weighted magnetic resonance imaging scan.

16. The method of claim 11, wherein using the gray scale values of the second image to calculate the pixels that correspond to a majority of the third component comprises statistically determining a threshold gray scale value above which a pixel will be deemed to contain the third component.

17. The method of claim 16, wherein the statistical determination includes comparison of a histogram of gray scale value of the pixels of the second image with a Gaussian distribution, and wherein the threshold gray scale value is determined to be that value that first exceeds the Guassian distribution.

18. The method of claim 11, wherein step (b) calculation includes dividing the first image into first pixels containing the third component, and second pixels free of the third component.

19. The method of claim 18, wherein the second pixels constitute a histogram, $H(G)$, of gray scale values of the first component and second component, wherein G constitutes a weighted average gray scale of a given pixel such that $G=y1 \times z/100+y3 \times (1-z/100)$, wherein the first component occupies z % of the pixel, and wherein the $H(G)$ is bounded by gray scale values $y1$ and $y3$, and wherein the number of pixels containing a majority of the first component equals:

$$\int_{y1}^{y3} H\left(y1 \times \frac{z}{100} + y3 \times \left(1 - \frac{z}{100}\right)\right) \times \frac{z}{100} \, dy.$$

20. The method of claim 18, wherein the first pixels have an upper gray scale value of y3, and second pixels with a gray scale greater than y3, X, are deemed to contain the third component.

21. The method of claim 20, wherein the first pixels constitute a histogram, $W(G)$, of gray scale values of the first component, the second component, and the third component, wherein G constitutes a weighted average gray scale of a given pixel such that $G=y1 \times z/100+y3 \times (1-z/100)$, wherein the third component occupies z % of the pixel, and wherein the $W(G)$ is bounded on its lower end by gray scale value y2, and wherein the number of pixels containing a majority of the third component equals:

$$\int_{y2}^{y3} W\left(y2 \times \left(1 - \frac{z}{100}\right) + y3 \times \frac{z}{100}\right) \times \frac{z}{100} \, dy.$$

22. The method of claim 21, wherein $W'(G)$ constitutes a histogram with the number of pixels containing a majority of the third component removed, wherein G constitutes a weighted average gray scale of a given pixel such that $G=y1 \times z/100+y3 \times (1-z/100)$, wherein the first component occupies z % of the pixel, and wherein the number of pixels containing a majority of the first component equals $$\int_{y1}^{y3} W'\left(y1 \times \frac{z}{100} + y3 \times \left(1 - \frac{z}{100}\right)\right) \times \frac{z}{100} \, dy.$$

23. The method of claim 22, wherein the first image contains N pixels, and wherein:
(a) the total number of pixels containing a majority of the third component equals X plus $$\int_{y2}^{y3} W\left(y2 \times \left(1 - \frac{z}{100}\right) + y3 \times \frac{z}{100}\right) \times \frac{z}{100} \, dy.$$

(b) the total number of pixels containing a majority of the first component equals $$\int_{y1}^{y3} H\left(y1 \times \frac{z}{100} + y3 \times \left(1 - \frac{z}{100}\right)\right) \times \frac{z}{100} \, dy \text{ plus}$$

$$\int_{y1}^{y3} W'\left(y1 \times \frac{z}{100} + y3 \times \left(1 - \frac{z}{100}\right)\right) \times \frac{z}{100} \, dy.$$

(c) the total number of pixels containing a majority of the second component equals N minus the sums of step (a) and step (b).

24. The method of claim 11, wherein the first and second images constitutes image slices of a particular volume of the tissue.

25. The method of claim 24, wherein the method is repeated for several different image slices each representing a different volume of the tissue.

26. The method of claim 25, wherein the first and second images obtained for each different volume of tissue are normalized to a uniform gray scale.

27. A method of determining the amount of a first component, a second component, and a third component in a tissue, the method utilizing a first image and a second image of the tissue, the images being comprised of N pixels wherein each pixel has a gray scale value, the method comprising:
(a) analyzing the second image to determine a threshold gray scale value, over which a pixel is deemed to contain the third component, and segregating the second image into first pixels containing the third component and second pixels free of the third component;
(b) segregating the first image into third pixels and fourth pixels corresponding respectively to the first pixels and second pixels of the second image, the third pixels containing gray scale values greater than y2, the fourth pixels containing gray scale values between y1 and y3, wherein y1<y2<y3, wherein the third pixels with a gray scale above y3 are deemed to be pixels containing the third component, X;
(c) analyzing the fourth pixels to segregate those pixels into pixels containing a majority of the first component, Y;

(d) analyzing the third pixels with gray scale values less than y3 to segregate fifth pixels, X', containing a majority of the third component;

(e) removing the fifth pixels from the third pixels, and analyzing the remaining third pixels to segregate those pixels containing a majority of the first component, Y';

wherein the number of pixels containing the third component is X+X', the number of pixels containing the second component is Y+Y', and the number of pixels containing the second component is N minus (X+X'+Y+Y').

28. The method of claim 27, wherein the tissue is a brain, the first component is white matter, the second components is gray matter, and the third matter is cerebral spinal fluid.

29. The method of claim 28, wherein the first and second images are pre-processed to remove all areas outside of and including a fatty layer that surrounds the brain.

30. The method of claim 27, wherein the first image is produced by a proton density magnetic resonance imaging scan, and the second image is produced by a T2-weighted magnetic resonance imaging scan.

31. The method of claim 27, wherein the step (a) includes comparison of a histogram of gray scale value of the pixels of the second image with a Gaussian distribution, and wherein the threshold gray scale value is determined to be that value that first exceeds the Guassian distribution.

32. The method of claim 27, wherein step (c) includes compiling a histogram, H(G), of gray scale values of the fourth pixels, wherein G constitutes a weighted average gray scale of a given pixel such that G=y1×z/100+y3×(1−z/100), wherein the first component occupies z % of the pixel, and wherein the pixels containing a majority of the first component, Y equals:

$$\int_{y1}^{y3} H\left(y1 \times \frac{z}{100} + y3 \times \left(1 - \frac{z}{100}\right)\right) \times \frac{z}{100}\, dy.$$

33. The method of claim 27, wherein step (d) includes compiling a histogram, W(G), of the gray scale values of the third pixels, wherein G constitutes a weighted average gray scale of a given pixel such that G=y1×z/100+y3×(1−z/100), wherein the third component occupies z % of the pixel, and wherein the number of pixels containing a majority of the third component, X', equals:

$$\int_{y2}^{y3} W\left(y2 \times \left(1 - \frac{z}{100}\right) + y3 \times \frac{z}{100}\right) \times \frac{z}{100}\, dy.$$

34. The method of claim 27, wherein step (e) include compiling a histogram W'(G) of the gray scale values of the remaining third pixels, wherein G constitutes a weighted average gray scale of a given pixel such that G=y1×z/100+y3×(1−z/100), wherein the first component occupies z % of the pixel, and wherein the number of pixels containing a majority of the first component equals $$\int_{y1}^{y3} W'\left(y1 \times \frac{z}{100} + y3 \times \left(1 - \frac{z}{100}\right)\right) \times \frac{z}{100}\, dy.$$

35. The method of claim 27, wherein the first and second images constitutes image slices of a particular volume of the tissue.

36. The method of claim 35, wherein the method is repeated for several different image slices each representing a different volume of the tissue.

37. The method of claim 36, wherein the first and second images obtained for each different volume of tissue are normalized to a uniform gray scale.

38. A method for producing a final image containing three different hues, wherein the final image contains pixels and is of a tissue containing mixed first, second, and third components, each hue corresponding to one of the components, the method comprising:

(a) taking a first image and a second image of the tissue, the first and second images containing pixels corresponding to pixels in the final image, wherein the first image accentuates the difference between the first and second components, and wherein the second image accentuates the differences between the third component and the first and second components;

(b) using the first and second images to calculate the pixels that containing a majority of the first component, the second component and the third component;

(c) displaying the final image by displaying the pixels that contain a majority of the first component in a first hue, displaying the pixels that contain a majority of the second component in a second hue, displaying the pixels that contain a majority of the third component in a third hue.

39. A method for segmenting the white matter, gray matter, and cerebral spinal fluid in an axial section of cerebrum comprising:

(a) acquiring a gray scale image of a proton-density scan and of a T2-weighted scan of the axial section;

(b) determining from the T2-weighted image which pixels of the image contain some cerebral spinal fluid;

(c) sectioning the pixels of the proton-density scan into a portion A containing only white and gray matter, a portion B containing white matter, gray matter, and cerebral spinal fluid, and a portion C containing only cerebral spinal fluid; calculating the number of pixels for the partial volume of white matter in portion A and B;

(d) calculating the number of pixels for the partial volume of cerebral spinal fluid in portion B, and C; and (e) calculating the number of pixels for the partial volume of gray matter by subtracting the number of pixels for white matter and cerebral spinal fluid from the total number of pixels.

40. The method of claim 39, wherein the pixels of the T2-weighted image that contain some cerebral spinal fluid are determined by producing a histogram of gray scale values from the T2-weighted image and statistically determining an appropriate threshold gray scale value, above which the pixels contain some cerebral spinal fluid.

41. The method of claim 40, where in the proton density image is divided into portions A, B, and C by:

(a) subtracting from the proton-density image the pixels spatially corresponding to the pixels of the T2-weighted scan which were found to contain some cerebral spinal fluid;

(b) producing a histogram H for the pixels of the proton-density image remaining when the pixels containing cerebral spinal fluid have been removed; producing a histogram W for the pixels of the proton-density image that corresponds to the pixels that contains some cerebral spinal fluid;

(c) determining from the histograms the lowest gray scale value that white matter can have $y_1$, the lowest gray scale value that cerebral spinal fluid containing pixels can have $y_2$, and the highest gray scale value that gray matter can have $y_3$; and defining A as H from $y_1$ to $y_3$, B as W from $y_2$ to $y_3$, and C as W from $y_3$ to the maximum gray scale value.

42. The method of claim 41, wherein the number of pixels for the partial volume of white matter in portion A is calculated by:
   (a) determining, for each gray scale value of H intermediate the $y_1$ and $y_3$, the percentage of white matter corresponding to that gray scale value; and
   (b) integrating a function over the range from the $y_1$ to $y_3$, said function being the total number of pixels at each gray scale value times the percentage of white matter corresponding to that gray value.

43. The method of claim 41, wherein the number of pixels corresponding to the partial volume of cerebral spinal fluid in section C is calculated by determining the total number of pixels in C.

44. The method of claim 41, wherein the number of pixels for the partial volume of cerebral spinal fluid in portion B is calculated by:
   (a) determining for each gray scale value of W intermediate $y_2$ to $y_3$, the percentage of cerebral spinal fluid corresponding to that gray scale value; and
   (b) integrating a function over the range from $y_2$ to $y_3$, said function being the total number of pixels at each gray scale value times the percentage of cerebral spinal fluid corresponding to that gray scale value.

45. The method according to claim 44, wherein the number of pixels for the partial volume of white matter in portion B is determined by:
   (a) removing from W the number of pixels corresponding to cerebral spinal fluid;
   (b) determining, for the resulting histogram W', for each gray scale value $y_2$ and $y_3$, the percentage of white matter corresponding to that gray scale value; and
   (c) integrating a function over the range from $y_2$ to $y_3$, said function being the total number of pixels at each gray scale value times the percentage of white matter corresponding to that gray scale value.

46. The method of claim 45, further comprising:
   (a) combining histograms H and W' to make a new histogram T;
   (b) calculating a threshold value t such that the number of pixels with a gray value less than t is the same as the number of pixels for the partial volume of white matter determined for sections A and B;
   (c) assigning a uniform hue to all pixels with a gray value less than t and a different uniform hue to all pixels with a gray scale value greater than t; and adding back into T the pixels corresponding to the partial volume of cerebral spinal fluid and assigning a third uniform hue to these pixels.

47. A method of determining the volumes of components in a human brain, said components being white matter, dark matter, and cerebral spinal fluid, the method comprising:
   (a) obtaining a gray scale image of a proton-density scan and of a T2-weighted scan of the brain, wherein each image comprises axial slices and for each axial slice of the proton-density image, there is a spatially corresponding slice of the T2-weighted image;
   (b) for an axial slice of the T2-weighted image determining which pixels of the slice contain some cerebral spinal fluid;
   (c) sectioning the pixels for the spatially corresponding slice of the proton-density scan into a portion A containing only white and gray matter, a portion B containing white matter, gray matter, and cerebral spinal fluid, and a portion C containing only cerebral spinal fluid;
   (d) calculating the number of pixels for the partial volume of white matter in portion A and B;
   (e) calculating the number of pixels for the partial volume of cerebral spinal fluid in portion B, and C;
   (f) calculating the number of pixels for the partial volume of gray matter by subtracting the number of pixels for white matter and cerebral spinal fluid from the total number of pixels;
   (g) repeating steps (a) through (f) for all of the axial slices of the two images; and
   (h) for each component, calculating the product of the number of pixels for the partial volume of the component times the width of a pixel time the length of a pixel times the thickness of a slice, and summing this product over all of the slices.

48. A method for segmenting the portions of the white matter, the gray matter and the cerebral spinal fluid and for calculating their respective volumes in a proton-density image and a T2-weighted image, photographed of an identical axial section of the part of the cerebrum, out of the slices provided by the magnetic resonance scanner, wherein said method comprises:
   (a) calculating the number of pixels constituting each of two mutually different components from the whole, taking into consideration of the ratio of the two;
   (b) deciding a threshold, on the basis of the numbers of pixels calculated in step (a), to segment the two portions in a region which has been blurred by the overlapping of two components;
   (c) removing the portion for the cerebrum from a proton-density image and also of removing the corresponding region from a T3-weighted image:
   (d) removing the portion for the brain and spinal cord from a T3-weighted image which has undergone step (c) and of eliminating the same region corresponding to that portion for the brain and spinal cord from a proton-density image;
   (e) of calculating the respective partial volume artifacts of the white matter and the gray matter in a proton-density image, whence the portion for the brain and spinal cord has been removed by step (a), leaving only the portions for the above two components; and,
   (f) calculating the respective volumes of the white matter and the gray matter by using the partial volume artifacts of the white matter and the gray matter as has been calculated in step (e) and also information on the slices provided by the computed tomography device.

49. A method for segmenting the portions for the white matter, the gray matter, and the cerebral spinal fluid and for calculating their respective volumes in a magnetic resonance image of the human brain according to claim 48, wherein step (c) comprises:
   (g) removing the dark background from a proton-density image of the human brain;
   (h) adjusting the distribution of gray values in a proton-density image so that the gray value distributions may be rendered similar with a view to making clear and certain the contrast between the gray values of the inner part of the brain and those of the fat layer encircling it in all slices;
   (i) segmenting and extracting the inner part of the brain from the cortex and fat layer which encircle it in a proton-density image, for which the gray values have been adjusted in Step (h); and, (j) segmenting the portion for the inner part of the brain in a corresponding T2-weighted image by the use of a proton-density image, where the inner part has been segmented.

50. A method of segmenting the portions for the white matter, the gray matter, and the cerebral spinal fluid and also for calculating their respective volumes in a magnetic resonance image according to claim 48, wherein step (d) is characterized in that the highest of all the gray values that overlap the Gaussian distribution curve after the histogram for a T2-weighted image of the inner region of the brain is sought and decided from the lowest gray value for the pixels representing the cerebral spinal fluid.

51. A method for segmenting the portions for the white matter, the gray matter, and the cerebral spinal fluid and also for calculating their respective volumes in a magnetic resonance image according to claim 48, wherein step (e) comprises:

(k) producing a first histogram, H, for a proton-density image, which contains only the white matter and the gray matter;

(l) calculating the partial volume artifact, PV1, of the white matter from the first histogram, H, produced in said step (k) above;

(m) producing a second histogram from the image, which remains after the part purely of the brain and spinal cord, has been removed from the image of the brain and spinal cord in the process of step (d):

(n) calculating the partial volume artifact, PV1, purely of the brain and spinal cord from the second histogram produced by said step (m) above;

(o) calculating the partial volume artifact, PV2, of the white matter in the region, whence said part purely of the brain and spinal cord has been removed;

(p) calculating the partial volume artifact of the gray matter by subtracting the sum of the partial volume artifacts (PV1+PV2) of the white matter, calculated by said steps (l) and (o) above, from the total number of pixel values of said first histogram;

(q) producing a third histogram including said first and second histograms;

(r) setting as the threshold the first gray value that the integral value of the distribution function, while it is being calculated increasing the gray value in said third histogram, gets a value for the first time larger than said sum (PV1+PV2) of the partial volume artifacts of the white matter; and, (s) producing an image where the white matter and the gray matter are segmented in each slice by the threshold set in said step (r) above.

52. A method for segmenting the portions for the white matter, the gray matter, and the cerebral spinal fluid and also for calculating their respective volumes in a magnetic resonance image according to claim 51, characterized in that in step (n), when, in a histogram W for the image of the brain and spinal cord mixed with the white matter and the gray matter after the part for pure brain and spinal cord has been removed from a proton-density image produced by step (e) the gray value y3 for the brain and spinal cord and the gray value y2 for the other component are extracted and the brain and spinal cord having the gray value of y3 occupies z % and the component other than the brain and spinal cord having the gray value of y2 occupies (100−z) % of the whole, then the gray value G which appears this time is calculated by the equation:

$$G = y2 \times \left(1 - \frac{z}{100}\right) + y3 \times \frac{z}{100}$$

and the total number of the pixels from the gray values y2 through y3 corresponding to the partial volume artifacts of the brain and spinal cord is calculated by the following equation:

$$PCSF2 = \int_{y2}^{y3} W\left(y2 \times \left(1 - \frac{z}{100}\right) + y3 \times \frac{z}{100}\right) \times \frac{z}{100} dy.$$

53. A method for segmenting the portions for the white matter, the gray matter, and the cerebral spinal fluid and also for calculating their respective volumes in a magnetic resonance image according to claim 51, characterized in that in step (o) W' is the distribution function of the histogram for the remaining part after the pixels for the partial volume artifact of the pure brain and spinal cord has been removed, the partial volume artifact of the white matter is calculated by the equation:

$$PV2 = \int_{y1}^{y3} W'\left(y1 \times \frac{z}{100} + y3 \times \left(1 - \frac{z}{100}\right)\right) \times \frac{z}{100} dy$$

54. A method for segmenting the portions for the white matter, the gray matter, and the cerebral spinal fluid and also for calculating their respective volumes in a magnetic resonance image according to claim 51, characterized in that in said step (l), the respective gray values purely of the white matter and of the gray matter, y1 and y2, are extracted by producing a histogram for the proton-density image, where the white matter and the gray matter alone are left behind in a slice of a certain thickness after the whole brain and spinal cord has been removed, and the gray value G which appears when the white matter having the gray value of y1 occupies z % and the gray matter having the gray value of y3 occupies (100−z) % of all in a certain thickness, is calculated by the following equation:

$$G = y1 \times \frac{z}{100} + y3 \times \left(1 - \frac{z}{100}\right)$$

and, by the method for calculating said z % as the pixels for the partial volume artifact of the white matter, in such a gray value, the sum total of the number of pixels for the partial volume artifact of the white matter of the gray values of y1 to y3 is calculated by the following equation:

$$PV1 = \int_{y1}^{y3} H\left(y1 \times \frac{z}{100} + y3 \times \left(1 - \frac{z}{100}\right)\right) \times \frac{z}{100} dy.$$

55. A method for segmenting the portions for the white matter, the gray matter, and the cerebral spinal fluid and also for calculating their respective volumes in a magnetic resonance image according to claim 48, characterized in that the number of slices containing the extracted white matter as N, the distance between slices as D, the number of pixels constituting the white matter extracted from the i-th slice as $L_p$, the horizontal length of a pixel as X, and the vertical length of a pixel as Y, and a slice number as $S_i$, the total volume of the white matter or the gray matter by the whole of the image slices produced by step (f) above is calculated by the following equation:

$$V = \sum_{i=1}^{N-1} \frac{(L_p \cdot X \cdot Y) \text{ of } S_i + (L_p \cdot X \cdot Y) \text{ of } S_{i+1}}{2} \cdot D.$$

* * * * *

UNITED STATES PATENT AND TRADEMARK OFFICE
CERTIFICATE OF CORRECTION

PATENT NO. : 6,895,107 B2  
DATED : May 17, 2005  
INVENTOR(S) : Jong-Won Park et al.

Page 1 of 1

It is certified that error appears in the above-identified patent and that said Letters Patent is hereby corrected as shown below:

<u>Title page,</u>
Item [73], Assignee, the country should be -- Korea --.

Signed and Sealed this

Eighteenth Day of October, 2005

JON W. DUDAS
*Director of the United States Patent and Trademark Office*